(12) United States Patent
Meloy

(10) Patent No.: US 7,450,985 B2
(45) Date of Patent: Nov. 11, 2008

(54) HEAD RESTRAINT SYSTEM FOR MEDICAL RESEARCH, DIAGNOSIS AND OPERATION

(76) Inventor: Mary Jane Meloy, 334 Westbourne St., La Jolla, CA (US) 92037

(*) Notice: Subject to any disclaimer, the term of this patent is extended or adjusted under 35 U.S.C. 154(b) by 0 days.

(21) Appl. No.: 11/804,006

(22) Filed: May 16, 2007

(65) Prior Publication Data
US 2007/0270683 A1 Nov. 22, 2007

Related U.S. Application Data

(60) Provisional application No. 60/800,709, filed on May 16, 2006.

(51) Int. Cl.
*A61B 5/05* (2006.01)
*A47B 7/00* (2006.01)
*A61F 5/37* (2006.01)

(52) U.S. Cl. .............. 600/422; 5/622; 128/870

(58) Field of Classification Search ............ 5/622, 5/636, 637; 128/870
See application file for complete search history.

(56) References Cited

U.S. PATENT DOCUMENTS

| 4,034,748 | A | * | 7/1977  | Winner ............ 602/19 |
| 4,182,322 | A | * | 1/1980  | Miller ............ 5/637 |
| 4,756,090 | A |   | 7/1988  | Pedrow |
| 4,916,765 | A |   | 4/1990  | Castronovo, Jr. |
| 5,400,787 | A |   | 3/1995  | Marandos |
| 5,619,996 | A |   | 4/1997  | Beresten |
| 6,128,797 | A | * | 10/2000 | Shaffer ............ 5/638 |

OTHER PUBLICATIONS http://www.additec.de/medtec/PRODUCTS/PATPOS/HEADNECK/FASTFIT.HTM (2004).

* cited by examiner

*Primary Examiner*—Patricia L Engle
*Assistant Examiner*—Jonathan J Liu
(74) *Attorney, Agent, or Firm*—Gordon & Rees LLP

(57) ABSTRACT

The present invention relates to a head restraint kit for use with a medical head device for immobilizing the head of a patient in medical research, diagnosis and operation. The head restraint kit is particularly suitable for use with a head coil for magnetic resonance imaging. The head restraint kit contains a head rest pillow for providing support to the head of a patient, a neck cushion for providing neck support, and one or more wedge cushions for providing further support for the head. The head restraint kit may also contain one or more compact square cushions which can be inserted into a space between the head and the medical head device for additional head support. The head restraint kit may further contain a cloth strap placed over the forehead of a patient for protecting and securing the head against movement.

5 Claims, 9 Drawing Sheets

HEAD RESTRAINT SYSTEM FOR MEDICAL RESEARCH, DIAGNOSIS AND OPERATION

CROSS-REFERENCE TO RELATED APPLICATION

This application claims the benefit of Provisional Patent Application Ser. No. 60/800,709, filed on May 16, 2006, of similar title.

TECHNICAL FIELD

The present invention relates to a head restraint kit for use with a medical head device for immobilizing the head of a patient during medical research, diagnosis or operation, particularly for use with a head coil for magnetic resonance imaging. The present invention also relates to a head restraint system which comprises a head restraint kit and a medical head device.

BACKGROUND OF THE INVENTION

In the field of neuroimaging, there is a significant impediment to collecting data from a subject while maintaining the subject immobilized during the data collection process. Neuroscientists and medical professionals routinely measure the brain's response to specific stimuli as a subject lies still with the head placed in a "helmet" like device known as a head coil. The subject is then moved into a Magnetic Resonance Imaging ("MRI") scanner. A subject is often required to lie still in the scanner for periods of up to 2 hours at a time with the subject's head in a "cage-like" helmet. The head coil which creates the sense of being placed in a cage over the head often causes anxiety in the subject because the head coil is very small and the subject often feels confined. If the subject moves his head, the data collected may have to be discarded because the measurements in an MRI scanner are extremely sensitive to such movement. This is a serious complication in the field of neurobiology. The costs for these procedures are high, and subject recruitment is difficult. If data from the MRI have to be discarded, information needed to analyze the results may be lost from the research studies or tests.

Accordingly, there is an urgent need for a head restraint system which is able to provide comfort to a subject, and convenience and versatility for its user. The present invention provides such a head restraint system, comprising a head restraint kit adapted for use with a restraint device such as a head coil. The head restraint kit of the present invention includes a head rest pillow for providing support to the head of a patient, a neck cushion for providing neck support, and one or more wedge cushions for providing further support for the head. The head restraint kit may also contain one or more compact square cushions which can be inserted into a space between the head and the head coil for additional head support. The head restraint kit further contains a cloth strap placed over the forehead of a patient for protecting and securing the head against movement. When used together with a head coil for MRI, a subject is able to hold still for the extended time period required for collecting data. When used appropriately, the head restraint kit provides support for both the head and neck of a subject for an extended period of time.

What was used Before the Present Invention

Although there are pillows used to restrain patient movement, these pillows are not effective at restraining movement, providing patient comfort or being adaptable to meet specific location constraints. For example, Newmatic Sound Systems (newmaticsound.com) offers foam-like pillows. In addition, some MRI manufacturers also provide their own foam products with their scanners. However, these pillows are either too small or too large and too stiff to help create the sense of support and comfort necessary for use with a head coil for immobilizing the head and neck of a subject for a long period of time without motion.

Furthermore, rubber items have been attempted for immobilizing a patient's head and neck. However, these rubber items often lead to pressure points on the subject's head, causing the subject to move during the procedures to try and alleviate this discomfort. In addition to using these rubber pads, other methods have been used to help a subject hold still in the MRI scanner, but none meet the objects of this head restraint system. One method is using a polyurethane product that is molded with hot water to create the shape of a mask that specifically fits the subject's face and head, known as a "Zorro" mask due to the way eye holes are created to fit the subject's face. These masks failed due to elevated feelings of claustrophobia and discomfort caused by having the material pressed against the face for long periods of time. Another method is to use a cervical collar made for patients with cervical injuries. It was hoped that by placing a subject in a restraining device that keeps his head and neck in a specific position, the subject would be unable to move. This approach also failed because the restraining device would press into the subject's neck and head causing pain and discomfort. This device had to be quickly removed, and left visible marks on the subject's skin where the collar was tightened. An additional method is to use a "bite bar" (medicalproductsdirect-.com), a device that attaches to the head coil over the subject's mouth and then the subject bites down on a rubber plate that is made from an impression taken of his mouth prior to entering the scanner. This device also failed in that the subject complained about having difficulty in swallowing as well as discomfort in the jaw and mouth. Inflatable bead bags have also been tried, but have failed due to skin discomfort, causing subjects to move. None of these aforementioned devices or methods have addressed the main issue, of securely supporting the head and neck while making a subject comfortable so that the subject will remain immobile for an extended period.

SUMMARY OF THE INVENTION

The present invention provides a head restraint kit for use with a medical head device such as a head coil (e.g., a 2-channel, 8-channel, or 12 channel head coil) for immobilizing a subject's head for an extended duration of time during research, medical diagnosis or operation procedures. The head restraint kit is particularly suitable for use with a head coil in magnetic resonance imaging. The head restraint kit contains a head rest pillow for providing support to the head of a patient, a neck cushion for providing neck support, and one or more wedge cushions for providing further support for the head. The head restraint kit may also contain one or more compact square cushions which can be inserted into a space between the head and the medical head device for additional head supports. The head restraint kit may further contain a cloth strap placed over the forehead of a patient to secure the head against movement.

The head restraint kit of the present invention is suitable for use with a head coil for MRI to provide support for both the head and neck of a subject during neuroimaging of the brain. Although this kit is developed for use with a specific MRI machine, all neuroimaging facilities can adapt the shapes and sizes of the pillow set to achieve their goal in supporting the head and neck of the subject or patient being imaged.

In the head restraint kit of the present invention, each individual pillow or cushion can independently be made from a variety of materials commonly used as pillow inserts, including feathers, goose down, polyester fiberfill, and foam forms, such as memory foams. Each foam pillow or cushion may be coated with a Dermalyte™ anti-soiling treatment. Such treatment protects the foam surfaces from contamination by blood, barium, iodine, etc. The coated pillows or cushions may be washed with aseptic solution or with alcohol. Each pillow or cushion may also have a pillow or cushion cover, which may be made from a variety of materials, including papers (disposable or non-disposable) and fabrics (disposable or nondisposable), such as chenille, denim, silk, fake fur, flannel, lace, leather, linen, suede, sunbrella, toile, ultrasuede, velvet, or vinyl.

The head restraint kit of the present invention may be used for all structural and functional neuroimaging technologies, for example, MRI and CT. Furthermore, the head restraint kit may also be used with head restraint devices in radiosurgery, such as gamma knife, Linac stereotactic radiosurgery, or cyberknife, for brain tumors.

DETAILED DESCRIPTION OF THE INVENTION

Figure 1:
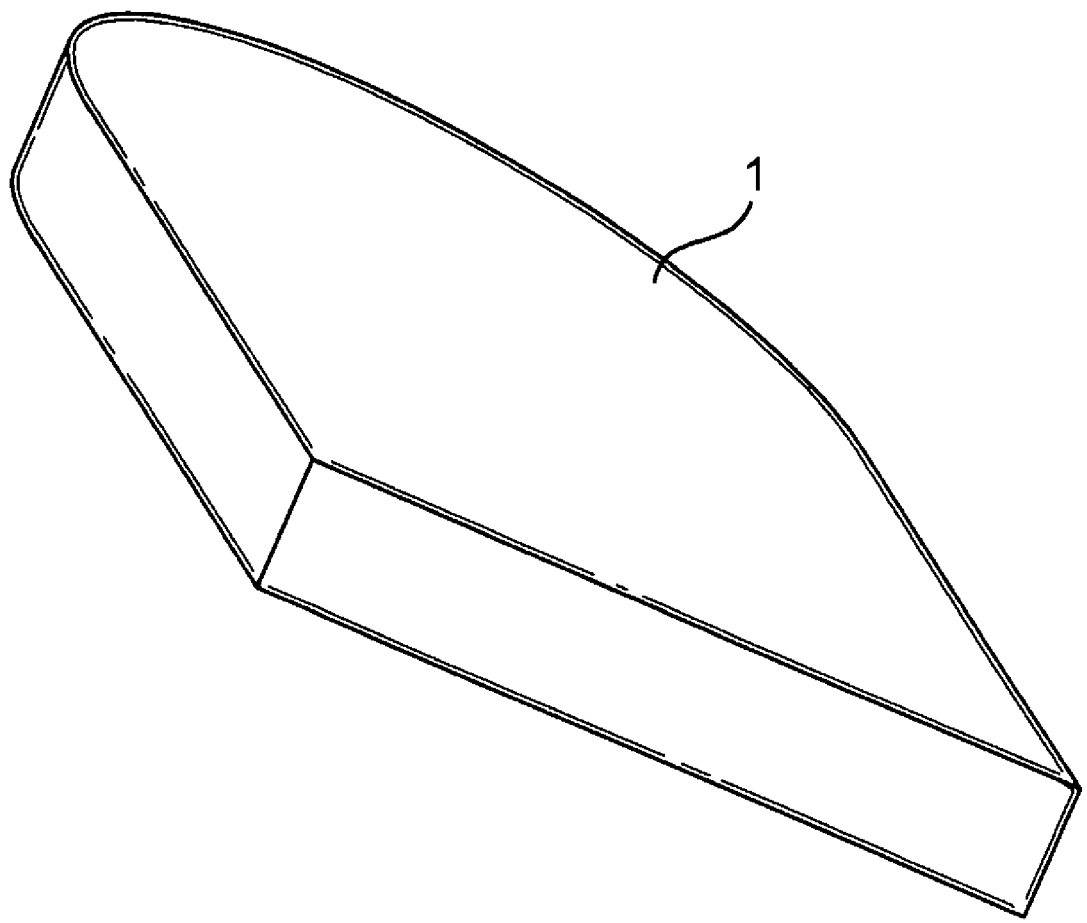
FIGS. 1 is a perspective view of a head rest pillow. according to the present invention.

FIG. 1 illustrates a head rest pillow 1, the first component of the head restraint kit of the present invention, head rest pillow 1 having a thickness from about 0.25 to about 2 inches and preferably about 0.5 inches; a width from about 4 to about 15 inches and preferably about 8.25 inches; and a length from about 6 to about 16 inches and preferably about 10.75 inches. A representative head rest pillow 1 is about 0.5 inches thick by about 8.25 inches wide by 10.75 inches long. In another representative example, the head rest pillow 1 is about 1 inch thick by about 14.75 inches wide by about 10.75 inches long. Head rest pillow 1 may be in any suitable shape, such as an arch, a circle, an oval, a semicircle, a square, a rectangle, or combinations thereof.

Figure 2:
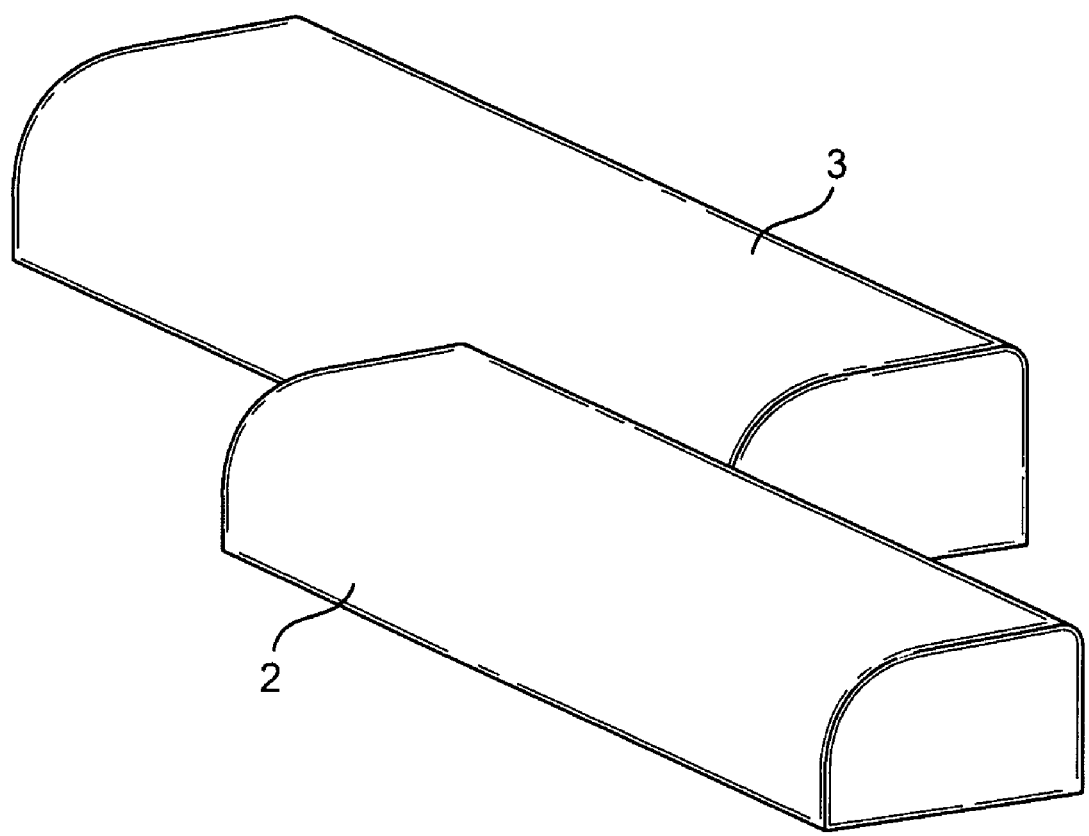
FIG. 2 illustrates a perspective view of two neck cushions according to the present invention;.

FIG. 2 illustrates neck cushions 2 and 3, the second component of the head restraint kit of the present invention, in two sizes. Neck cushion 2 is the smaller of the two cushions shown, having a range of measurements ranging from about 1.0 to about 1.5 inches thick, by from about 2.5 to about 3.5 inches wide, and by about 4.0 to about 9.0 inches long; with a representative range of measurements being about 1.25 inches thick by about 2.5 inches wide by about 6.0 inches long. In general, neck cushion 2 is elongated and has two sides. Each side may be in any suitable shape, such as an arch, a circle, an oval, a semicircle, a square, a rectangle, or combinations thereof.

Neck cushion 3 has a range of measurements from about 1.5 to about 2.0 inches thick, by from about 2.5 to about 3.5 inches wide, by about 4.5 to about 9.5 inches long; with a representative range of measurements of about 1.5 inches thick by about 2.5 inches wide by about 6.25 inches long.

Figure 3:
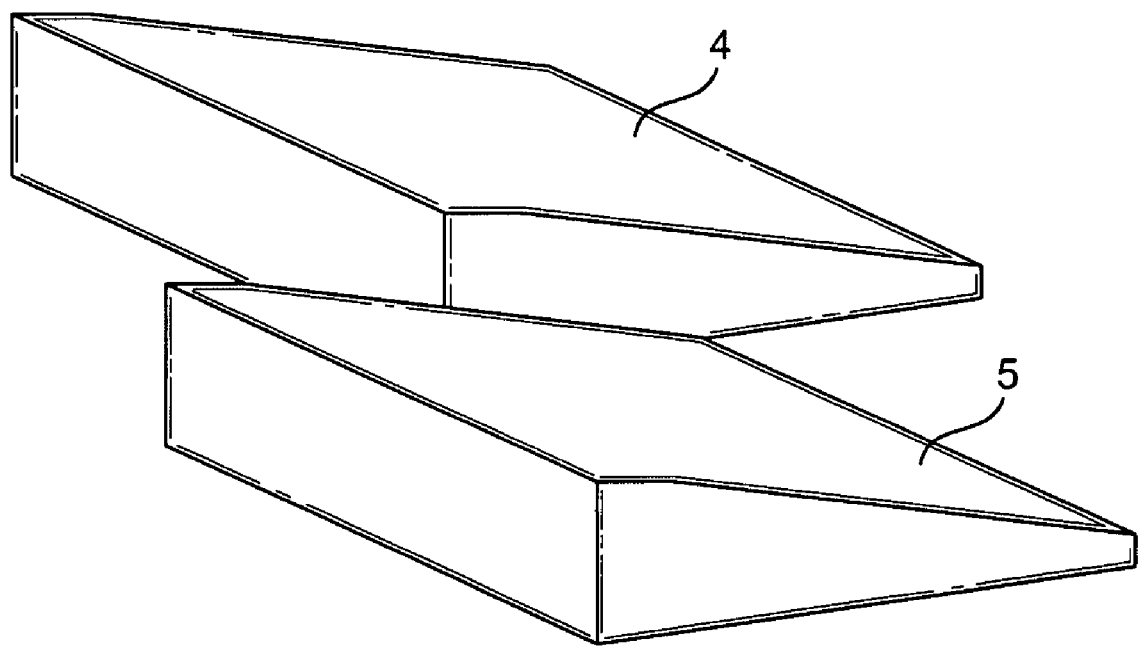
FIG. 3 illustrates a perspective view of two wedge cushions according to the present invention;.

FIG. 3 illustrates support wedge cushions 4 and 5. Each wedge cushion may have a thickness from about 0.01 to 1 inch on the smaller end and about 1.0 to about 4.0 inches on the taller end, by about 3 to about 7 inches wide, and by about 3 to about 7 inches long. In one representative example, the wedge is about 0.25 inches on the smaller end and about 1.25 inches on the taller end of the thickness, by about 4.0 inches wide by about 4.0 inches long. In another representative example, the wedge is about 0.5 inches on the smaller end and about 2.25 inches on the taller end of the thickness, by about 4.0 inches wide by about 4.0 inches long. In yet another representative example, the wedge cushion is about 0.5 inches on the smaller end and about 2.25 inches on the taller end of the thickness, by about 5.0 inches wide by about 5.0 inches long. In general, the side wedge cushion is in a rectangular or square shape. However, it may also be in any other suitable shape, such as an arch, a circle, an oval, a semicircle, or combinations thereof. When there are two or more wedge cushions, they may be the same or different in size or shape. Support wedge cushions 4 and 5 are dimensioned to hold headphones in place about a patient's head during a measurement session.

Figure 4:
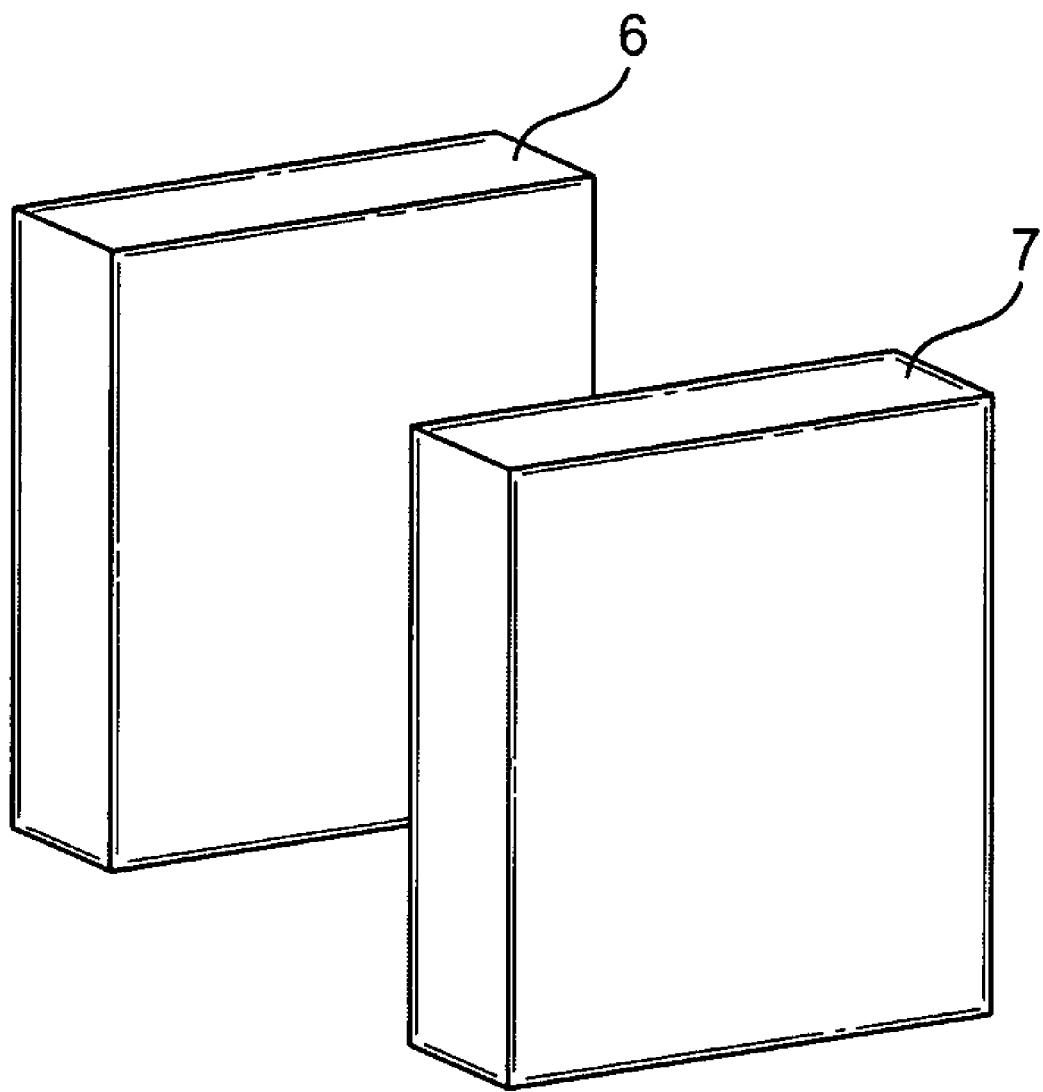
FIG. 4 illustrates a perspective view of two compact cushions according to the present invention;.

FIG. 4 illustrates two compact cushions, 6 and 7, the fourth component of the head restraint kit of the present invention, intended to provide added support to accommodate all head sizes with a range of measurements about 0.5 to about 3 inches, preferably about 0.5 to about 1 inch thick, by about 3.5 to about 5.0 inches wide, and by about 2.0 to about 8.0 inches long. In one representative example, the square cushion is about 0.75 inches thick by about 4.0 inches wide and by 4.0 inches long. In another representative example, the square cushion is about 1.75 inches thick by about 4.0 inches wide by 4.0 inches long. In general, the compact cushion is a rectangular or square shape. However, it may also be in any other suitable shape, such as an arch, a circle, an oval, a semicircle, or combinations thereof. When there are two or more compact cushions, they may be the same or different in size or shape.

Figure 5:
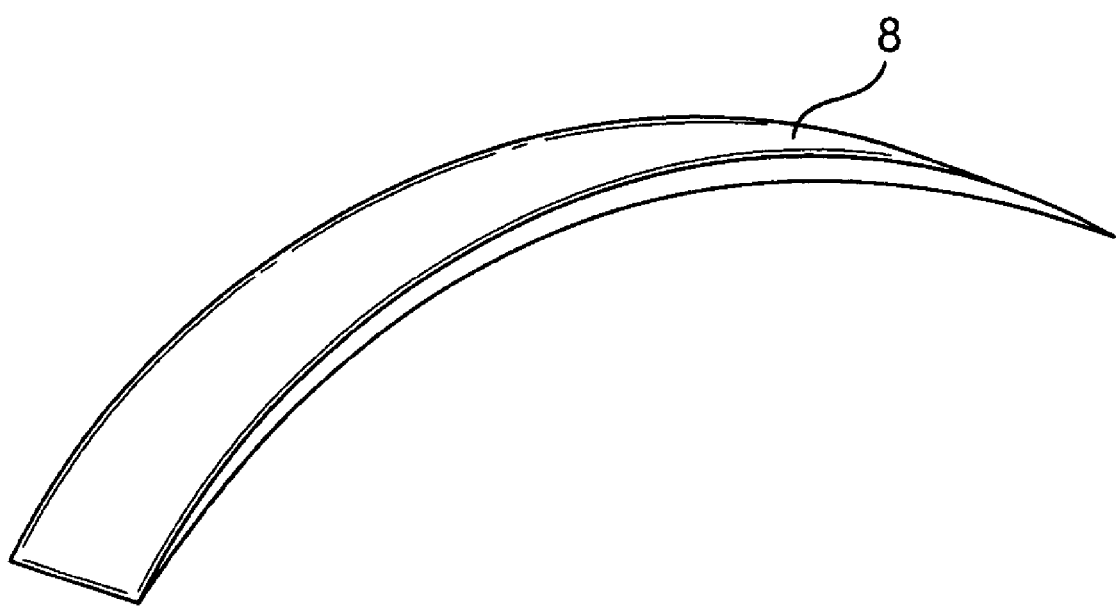
FIG. 5 is a perspective view of a head strap according to the present invention;.

FIG. 5 illustrates the fifth component, head strap 8, that is secured with tape and placed over the forehead of a subject to protect the skin and hair. Head strap 8 also serves as sensory feedback, reminding the subject where to keep his head during the scanning session. Head strap 8 has a measurement range from about 1 to about 2 inches wide and about 10 to about 20 inches long; with a representative measurements of being about 1.5 inches wide by about 14 inches long.

Figure 6:
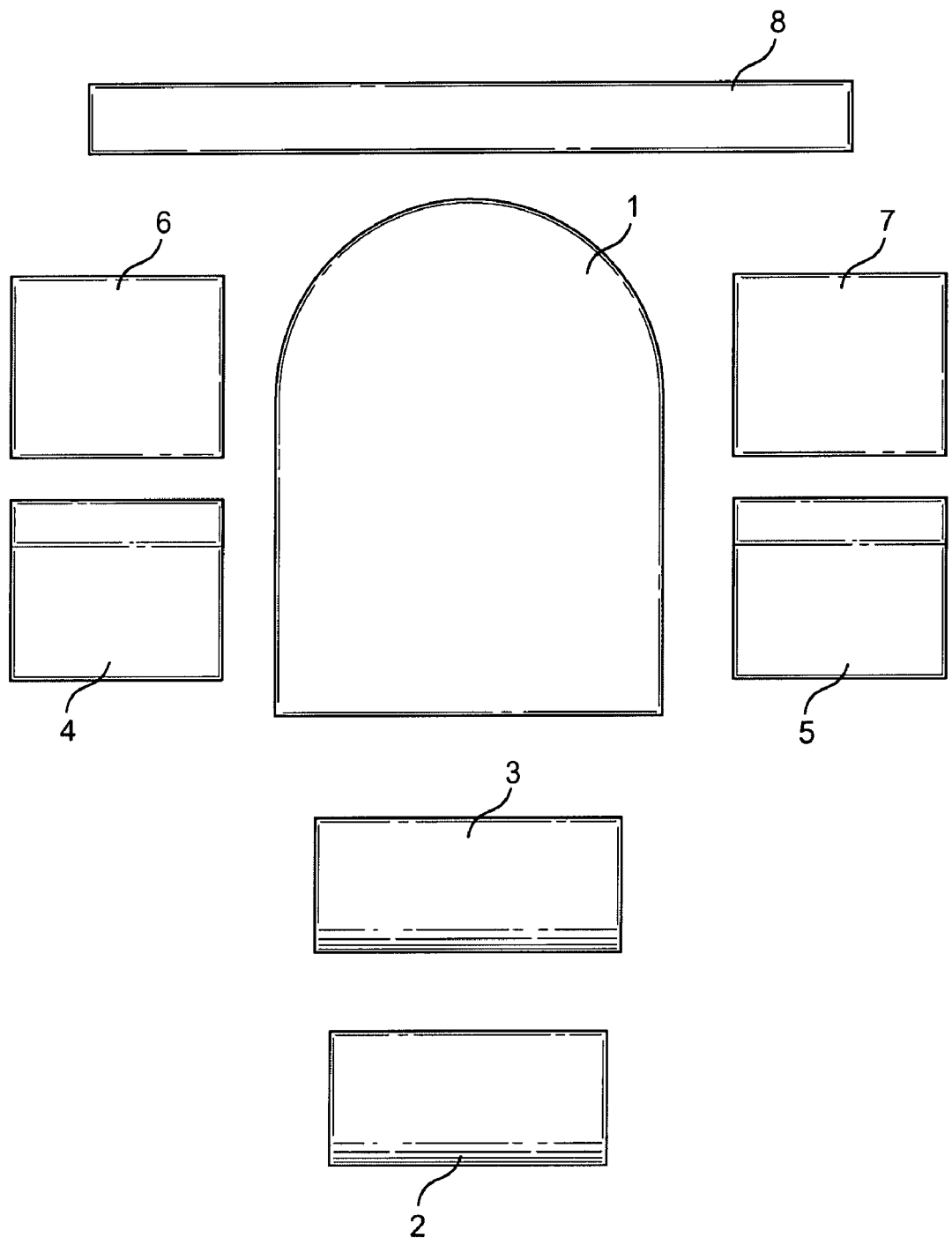
FIG. 6 is a perspective view of a head restraint kit according to an embodiment of the present invention, the head restraint kit comprising containing a head rest pillow, two neck cushions, two wedge cushions, two compact cushions, and a head strap;.

FIG. 6 illustrates the full complement of pillows that comprise the head restraint kit of the invention. The subject lays his or her head on the head rest pillow 1, with either or both of neck cushions 2 and 3 being used to support the neck. Either or both of support wedge cushions 4 and 5 are positioned to hold the necessary headphones in place without pushing on the subject's face. Either or both of compact cushions 6 and 7 provide added support to accommodate all head sizes, and head strap 8 protects the patient's skin and hair.

Figure 7:
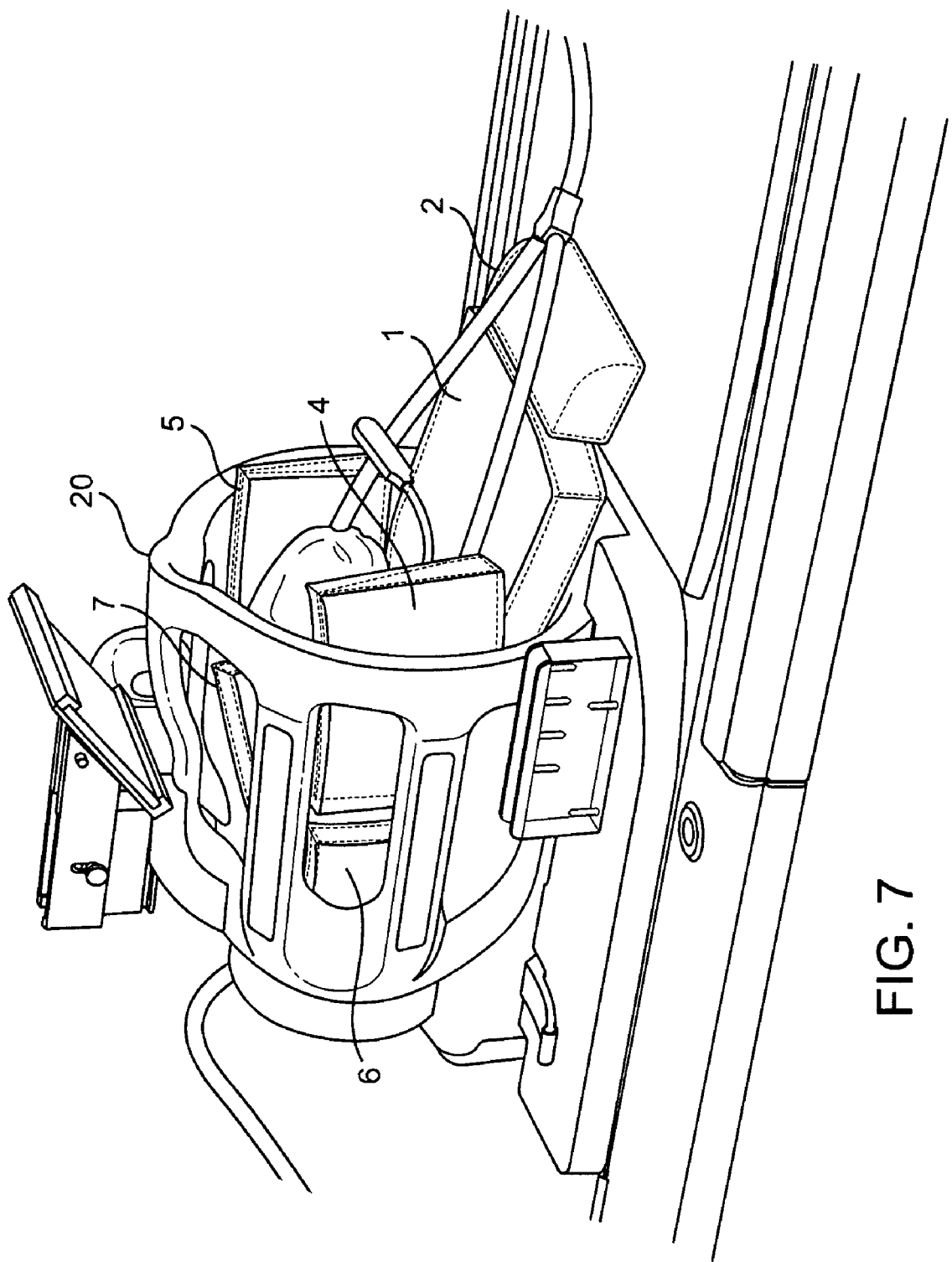
FIG. 7 is a perspective view of an MRI head coil. in which a head restraint kit according to the present invention is placed, the pillows being depicted within covers.

FIG. 7 depicts the pillows of the head restraint kit positioned within head coil 20 prior to the patient's head being positioned therein for measurement.

Figure 8:
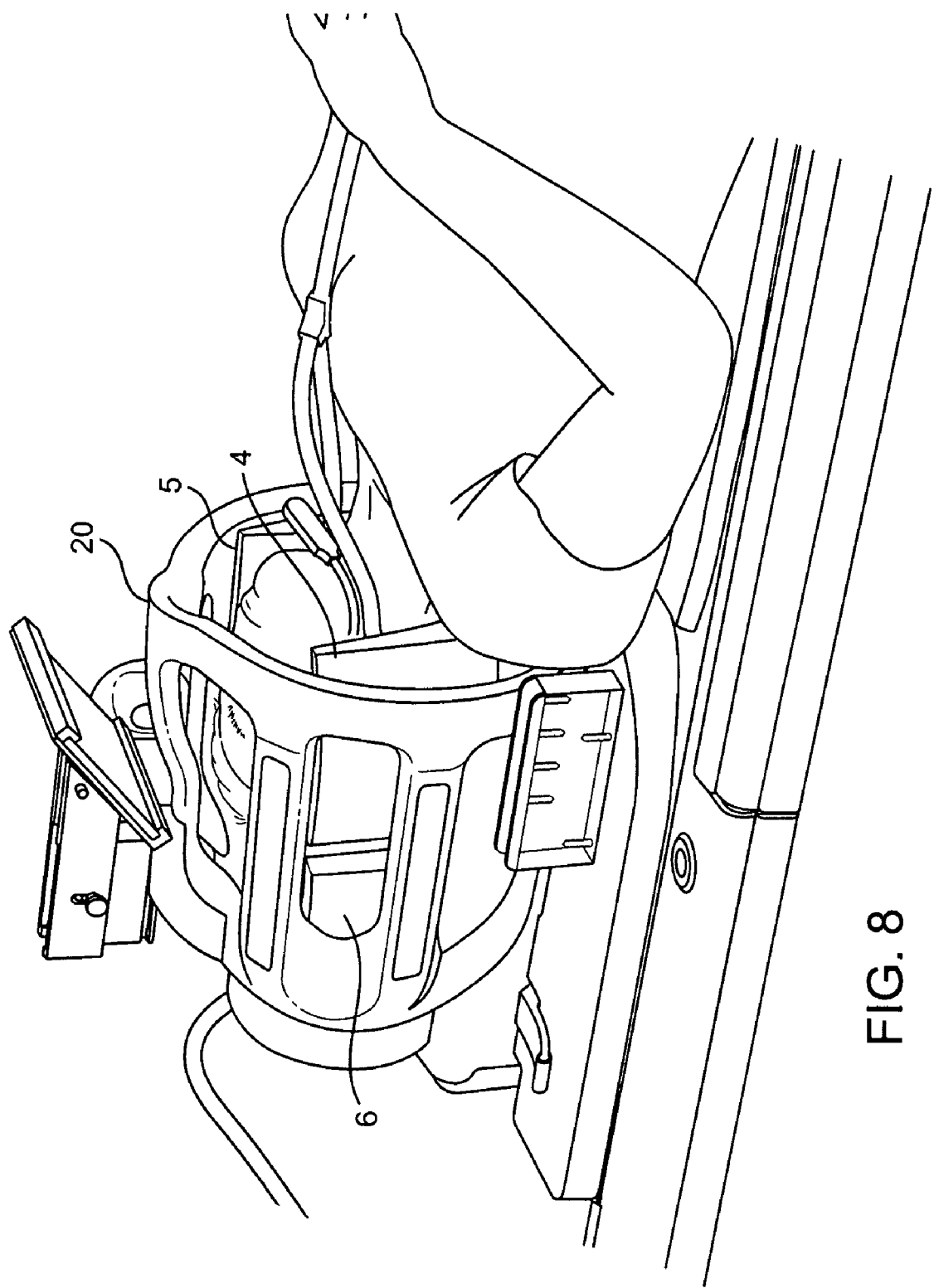
FIG. 8 is a perspective view of a head restraint kit according to the present invention in use and disposed within an MRI a head coil, the pillows being depicted uncovered;.

FIG. 8 depicts the pillows of the head restraint kit positioned within head coil 20 and about a patient's head.

Figure 9:
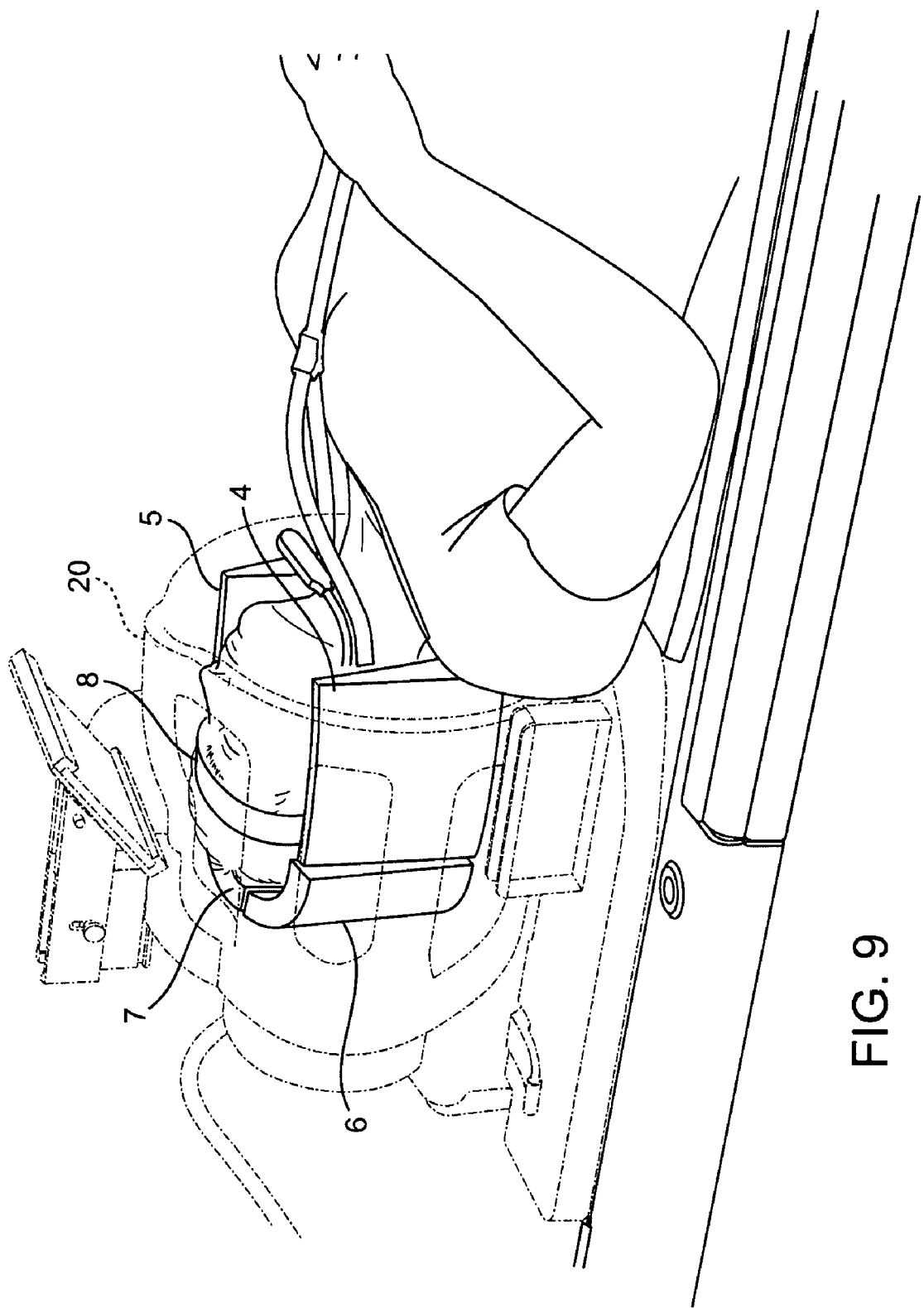
FIG. 9 is a perspective view of a head restraint kit according to the present invention as used in use within an MRI head coil.

FIG. 9 depicts a representative positioning of the pillows of the head restraint kit about a patient's head within head coil 20, as depicted in FIG. 8, head coil 20 being illustrated by dotted lines.

In one embodiment of the present invention, the pillow and cushions in the head restraint kit are made from memory foam. Memory foam is also known as viscoelastic polyurethane foam, and is made from polyurethane with additional chemicals that add to its viscosity level, thereby increasing the density of the foam. Depending on the chemicals used and the overall density of the foam, memory foam can be firmer in cooler temperatures and softer in warmer environments. Higher density memory foam can react with body heat and allow it to mold itself to the shape of a warm body within a few minutes. However, a lower density memory foam is pressure-sensitive and will mold more quickly to the shape of the body. The memory foam used in the present invention may have various densities, including both high and low density memory foam.

The memory foam is soft enough to provide comfort to the subject, and yet firm enough to ensure the positioning of the head in the MRI scanner.

The examples set forth above are provided to give those of ordinary skill in the art with a complete disclosure and description of how to make and use the preferred embodiments of the head restraint kit and system, and are not intended to limit the scope of what the inventor regards as her invention. Modifications of the above-described modes for carrying out the invention that are obvious to persons of skill in the art are intended to be within the scope of the following claims. All publications, patents, and patent applications cited in this specification are incorporated herein by references as if each such publication, patent or patent application were specifically and individually indicated to be incorporated herein by reference.

What is claimed is:

1. A neuroimaging head coil and head restraint cushion assembly, comprising:
    a neuroimaging head coil having an inner bottom and side surfaces;
    a head rest pillow, comprising:
        a curved first end positioned on top of the inner bottom surface of the neuroimaging head coil;
        a flat second end positioned outside the neuroimaging head coil; and
        first and second parallel side walls extending from the curved first end to the flat second end, wherein the first and second side walls extend from inside the neuroimaging head coil to outside the neuroimaging head coil;
    a neck cushion positioned outside the neuroimaging head coil adjacent to the flat second end of the head rest pillow, the neck cushion having a curved top surface for providing neck support;
    two flat-faced wedge cushions positioned at least partially inside the neuroimaging head coil for holding headphones against a patient's head, wherein each wedge cushion is wedge-shaped having a first end thicker than a second end opposite the first end, wherein the first end of a first wedge cushion is adjacent to the first side wall of the head rest pillow, and wherein the first end of a second wedge cushion is adjacent to the second side wall of the head rest pillow;
    a first compact cushion positioned inside the neuroimaging head coil adjacent to the first side wall of the head rest pillow and adjacent to the first wedge cushion to cradle side and top portions of a patient's head;
    a second compact cushion positioned inside the neuroimaging head coil adjacent to the second side wall of the head rest pillow and adjacent to the second wedge cushion to cradle side and top portions of a patient's head; and
    a sensory feedback head strap adhered to the neuroimaging head coil and placed over a forehead of a patient to remind the patient of a preferred head position within the neuroimaging head coil.

2. The neuroimaging head coil and head restraint cushion assembly of claim 1, wherein said first and second compact cushions are rectangular.

3. The neuroimaging head coil and head restraint cushion assembly of claim 1, wherein said first and second compact cushions are square.

4. The neuroimaging head coil and head restraint cushion assembly of claim 1, wherein the pillow and cushions further comprise an anti-soiling coating.

5. The neuroimaging head coil and head restraint cushion assembly of claim 1, wherein the neuroimaging head coil is a magnetic resonance imaging head coil.

* * * * *